(12) United States Patent
Leong et al.

(10) Patent No.: US 6,794,176 B1
(45) Date of Patent: Sep. 21, 2004

(54) **CULTIVAR SPECIFICITY GENE FROM THE RICE PATHOGEN *MAGNAPORTHE GRISEA*, AND METHODS OF USE**

(75) Inventors: Sally A. Leong, Avoca, WI (US); Mark L. Farman, Lexington, KY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/257,585

(22) Filed: Feb. 25, 1999

Related U.S. Application Data

(60) Provisional application No. 60/075,925, filed on Feb. 25, 1998.

(51) Int. Cl.[7] .............................. C12N 1/21; C12N 1/15; C12N 15/29
(52) U.S. Cl. ................. 435/252.3; 536/23.6; 435/320.1
(58) Field of Search ........................... 435/320.1, 252.3, 435/69.1, 419, 254.11, 348, 468, 471, 455; 536/23.7, 23.74; 800/278, 279, 298, 301, 320.2

(56) References Cited

PUBLICATIONS

Gopalan et al, 1996, Plant Cell 8:1095–1105.*
Jia et al, 2000, EMBO J. 19:4004–4014.*
Sweigard et al, 1995, Plant Cell 7:1221–1233.*
Joosten et al, 1997, Plant Cell 9:367–379.*
Rohe et al., The race–specific elicitor, NIP1, from the barley pathogen, *Rhynchosporium sexalis* 1995 The EMBO Journal vol. 14, No. 17, pp. 4168–4177.*
Farman et al., Analysis of the Structure of the AVR–CO39 Avirulence Locus in Virulent Rice–Infecting Isolates of *Magnaporthe grisea*, 2002, MPMI, vol. 15, No. 1, pp. 6–16.*

Shimizu T, et al. "An upstream regulatory sequence stimulates expression of the perfringolysin O gene of Clostridium perfringens." Infec. Immun. 59: 137–142, Jan. 1991.*
Liew, C.C., et al., "K5827F fetal heart, lambda ZAP express Homo sapiens cDNA clone K5827 5' similar to EST (EST07299)," EMBL Accession No. N88845, Jul. 25, 1996, XP–002107756, 1 page.
Seogchan Kang, et al. The PWL Host Specificity Gene Family in the Blast Fungus *Magnaporthe grisea*. *Molecular Plant–Microbe Interactions*. 1995 8: 939–948.
S.A. Leong, et al. Genetic and molecular anaylsis of a cultivar specificty locus from the rice blast fungus *Magnaprothe grisea*. *Rice Genetics III, Proceedings of the Third Annual Rice Genetics Symposium*. 1996: 846–852.
N. Nita, et al. Genome organization of *Magnaporthe grisea*: integration of genetic maps, clustering of transposable elements and identification of genome duplications and rearrangements. *Theor Appl Genet*. 1997 95: 20–32.
J. R. Smith and S. A. Leong. Mapping of a *Magnaporthe grisea* locus affecting rice (Oryza sativa) cultivar specificity. *Theo Appl Genet*. 1994 88: 901–908.
J. A. Sweigard, et al. Genetic map of the rice blast fungus *Magnaporthe grisea* (n=7). *Genetic Maps*. 1993 6: 3.112–3.115.
Barbara Valent, et al. *Magnaporthe grisea* Genes for Pathogenicity and Virulence Identified Through a Series of Backcrosses. *Genetics Society of America*. 1991 127: 87–101.

* cited by examiner

*Primary Examiner*—Amy J. Nelson
*Assistant Examiner*—Anne Kubelik
(74) *Attorney, Agent, or Firm*—Woodcock Washburn LLP

(57) ABSTRACT

This invention provides a novel avirulence gene from the rice blast pathogen, *Magnaporthe grisea*. The gene, AVR1-CO39, confers cultivar-specific avirulence to strains of *M. grisea* that carry the gene. Also disclosed are methods of using the gene and its encoded products for improving resistance of rice to the rice blast pathogen.

7 Claims, No Drawings

CULTIVAR SPECIFICITY GENE FROM THE RICE PATHOGEN *MAGNAPORTHE GRISEA*, AND METHODS OF USE

This application claims the benefit of priority of U.S. Provisional Application No. 60/075,925, filed on Feb. 25, 1998, the contents of which are incorporated by reference herein its entirety.

Pursuant to 35 U.S.C. §202(c), it is acknowledged that the U.S. Government has certain rights in the invention described herein, which was made in part with funds from the United States Department of Agriculture, Grant Nos. 58-3655-3-107 and 58-3655-4-140, and from the National Institutes of Health, Grant No. GM33716-08S1.

FIELD OF THE INVENTION

This invention relates to the field of disease resistance in plants. In particular, the invention provides a novel avirulence gene from the rice blast pathogen, *Magnaporthe grisea*, and methods of using the gene and its encoded products for improving resistance of rice to this pathogen.

BACKGROUND OF THE INVENTION

Rice is a major staple food for about two-thirds of the world's population. More than ninety percent of the world's rice is grown and consumed in developing countries. Rice blast disease, caused by the fungus *Magnaporthe grisea*, threatens rice crops worldwide. The disease can cause yield losses of ten to thirty percent in infested fields. Rice blast has been an ongoing problem in rice growing areas of the southern United States. It has now become a significant problem in rice growing areas of California, as well.

The "gene-for-gene" hypothesis has been advanced to explain the very specific disease resistance/susceptibility relationship that often exists between races of a plant pathogen and cultivars of its host species. The gene-for-gene hypothesis has been found applicable to many host-pathogen interactions, including that of the rice blast fungus, *Magnaporthe grisea*, and its host, *Oryza sativa*. To be able to understand and manipulate this host-pathogen relationship is of great practical interest as *M. grisea* is rapidly able to overcome new disease resistance in rice soon after their deployment. Moreover, *M. grisea* exists as a complex genus with many subspecific groups that are infertile, but differ in their host range. How these different subspecific groups interrelate evolutionarily is of great concern to plant breeders since some of these alternate hosts are frequently found growing in close proximity to, or in rotation with rice, and *M. grisea* isolates infecting these alternate hosts can sometimes also infect rice.

Gene-for-gene resistance (also known as hypersensitive resistance (HR) or race-specific resistance) depends for its activation on specific recognition of the invading pathogen by the plant. Many individual plant genes have been identified that control gene-for-gene resistance. These genes are referred to as resistance (R) genes. The function of a particular R gene depends on the genotype of the pathogen. A pathogen gene is referred to as an Avr gene if its expression causes the pathogen to produce a signal that triggers a strong defense response in a plant having a corresponding R gene. This response is not observed in the absence of either the Avr gene in the pathogen or the corresponding R gene in the plant. It should be noted that a single plant may have many R genes, and a single pathogen may have many Avr genes. However, strong resistance occurs only when an Avr gene and its specific R gene are matched in a host-pathogen interaction. In this instance, resistance generally occurs as activation of a HR response, in which the cells in the immediate vicinity of the infection undergo programmed necrosis in order to prevent the further advance of the pathogen into living plant tissue. Other features of the resistance response may also include synthesis of antimicrobial metabolites or pathogen-inhibiting enzymes, reinforcement of plant cell walls in the infected area, and induction of signal transduction pathways leading to systemic acquired resistance (SAR) in the plant.

The molecular basis of host-cultivar specificity and pathogenic variability in *M. grisea* is only beginning to be elucidated with the identification, mapping and, in some instances, cloning of specific Avr genes from pathogenic isolates of *M. grisea*. For instance, AVR2-YAMO (cultivar specificity) and PWL2 (host specificity) (Valent & Chumley, pp. 3.113–3.134 in *Rice Blast Disease* (R. Zeigler, S. A. Leong, P. Teng, Eds.), Wallingford: CAB International, 1994) both function as classic avirulence genes by preventing infection of a specific cultivar or host. AVR2-YAMO encodes a 223-amino acid protein with homology to proteases, while PWL2 encodes a 145-amino acid polypeptide which is glycine-rich. Based on the predicted amino acid sequences of the proteins, both may be secreted.

Homologs of both AVR2-YAMO and PWL2 appear to be widely distributed in rice and in other grass-infecting isolates of *M. grisea*, thereby confirming that *M. grisea* isolates which do not infect rice still may carry host or cultivar specificity genes for rice. In some cases, homologs of AVR2-YAMO and PWL2 have been shown to be functional and to exhibit the same host or cultivar specificity as AVR2-YAMO or PWL2.

As another example of a potentially useful Avr gene, the cultivar specificity gene AVR1-CO39, which determines avirulence on rice cultivar CO39, has been identified (Valent et al., Genetics 127: 87–101, 1991) and mapped to a position on *M. grisea* chromosome 1 (Smith & Leong, Theor. Appl. Genet. 88: 901–908, 1994). A segment of chromosome 1 that appears to contain the AVR1-CO39 gene has been isolated and cloned into a cosmid vector (Leong et al., pp. 846–852 in *Rice Genetics III, Proceedings of the Third Annual Rice Genetics Symposium*, G. S. Khush, Ed., Island Harbor Press, Manila, 1996); however, the gene itself heretofore has not been identified and characterized.

The availability of cloned cultivar and host specificity genes from *M. grisea* and, ultimately, the corresponding R genes from rice provides useful tools for manipulating and augmenting resistance to this pathogen in the field. Accordingly, it is an object of the present invention to provide a new cloned *M. grisea* cultivar specificity gene, AVR1-CO39, and its functional homologs for such use.

SUMMARY OF THE INVENTION

According to one aspect of the invention, there is provided an isolated nucleic acid, AVR1-CO39, from *Magnaporthe grisea* that confers rice cultivar CO39-specific avirulence to fungal plant pathogens that contain the nucleic acid. The nucleic acid preferably comprises part or all of Sequence I.D. No. 1, or hybridizes with part or all of Sequence I.D. No. 1 or its complement.

According to another aspect of the invention, there is provided a polypeptide encoded by part or all of the isolated nucleic acid of claim 1. Preferably, the polypeptide is selected from the group of polypeptides encoded by ORFS 1, 2, 3, 4, 5, 6 and 7, corresponding to Sequence ID No's. 2, 3, 4, 5, 6, 7 and 8, respectively, and most preferably is encoded by ORF 3.

According to another aspect of the invention, a transgenic epiphytic bacterium is provided, which expresses a portion of an AVR1-CO39 gene effective to confer rice cultivar CO39-specific avirulence to microorganisms expressing the gene. Preferably, the transgenic epiphytic bacterium expresses ORF3 of Sequence ID No. 1, or a functional equivalent.

According to another aspect of the invention, a method of enhancing the scope of resistance of rice cultivar CO39 plants to pathogenic microorganisms is provided. The method comprises treating the plants with an epiphytic bacterium that expresses a portion of an AVR1-CO39 gene effective to trigger expression of a CO39-specific R gene in the plants.

According to another aspect of the invention, a second method of enhancing the scope of resistance of rice cultivar CO39 plants to pathogenic microorganisms is provided. This method comprises treating the plants with a protein extract comprising polypeptides produced by expression of AVR1-CO39, in an amount effective to trigger expression of a CO39-specific R gene in the plants.

These and other features and advantages of the present invention will be described in greater detail in the description and examples set forth below.

DETAILED DESCRIPTION OF THE INVENTION

I. Definitions

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "pathogen-inoculated" refers to the inoculation of a plant with a pathogen.

The term "disease defense response" refers to a change in metabolism, biosynthetic activity or gene expression that enhances the plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase. Such defense responses appear to be induced in plants by several signal transduction pathways involving secondary defense signaling molecules produced in plants. Agents that induce disease defense responses in plants include, but are not limited to: (1) microbial pathogens, such as fungi, bacteria and viruses; (2) microbial components and other defense response elicitors, such as proteins and protein fragments, small peptides, β-glucans, elicitins and harpins, cryptogein and oligosaccharides; and (3) secondary defense signaling molecules produced by the plant, such as salicylic acid, $H_2O_2$, ethylene and jasmonates.

The term "promoter region" refers to the 5' regulatory regions of a gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1998.

II. Description of AVR1-CO39 and its Encoded Peptides

In accordance with the present invention, a novel *Magnaporthe grisea* avirulence gene has been isolated and cloned. This gene is referred to herein as AVR1-CO39, to denote its function as a gene that confers cultivar-specific interactions with rice cultivar CO39. The cloning of an AVR1-CO39 gene from *M. grisea* strain 2539 and analysis of the gene are described in detail in Example 1. The gene contains four open reading frames, one of which (ORF3) appears to play the most key role in conferring cultivar specific avirulence to Magnaporthe isolates that carry the gene. Homologs of the strain 2539 isolate AVR1CO39 gene have been identified in a diverse array of other Magnaporthe isolates.

A genomic clone of AVR1-CO39 from *M. grisea* strain 2539, an exemplary AVR1-CO39 of the invention, is described in detail herein and its nucleotide sequence is set forth in Example 1 as Sequence I.D. No. 1. Sequence I.D. No. 1 contains four open reading frames. It is believed that one or more of these open reading frames are responsible for conferring avirulence on cultivar CO39, either by virtue of the gene product expressed from the open reading frame or by possession of critical transcription or translation regulatory sequences (see Example 1).

Although a genomic clone of AVR1-CO39 from *M. grisea* isolate 2539 is described and exemplified herein, this invention is intended to encompass nucleic acid sequences and proteins from other Magnaporthe isolates that are sufficiently similar to be used instead of the isolate 2539 AVR1-CO39 nucleic acid and proteins for the purposes described below. These include, but are not limited to, allelic variants and natural mutants of Sequence I.D. No. 1, which are likely to be found in any given population of Magnaporthe isolates. Because such variants are expected to possess certain differences in nucleotide and amino acid sequence, this invention provides an isolated AVR1-CO39 nucleic acid molecule having at least about 60% (preferably 70% and more preferably over 80%) sequence homology in the coding regions with the nucleotide sequence set forth as Sequence I.D. No. 1 (and, most preferably, specifically comprising the coding region of sequence I.D. No. 1). This invention also provides isolated polypeptide products of the open reading frames of Sequence I.D. No. 1, having at least about 60% (preferably 70% or 80% or greater) sequence homology with the amino acid sequences of Sequence I.D. No's. 2, 3, 4, 5, 6 or 7, respectively. Because of the natural sequence variation likely to exist among AVR1-CO39 genes, one skilled in the art would expect to find up to about 30–40% nucleotide sequence variation, while still maintaining the unique properties of the AVR1-CO39 gene and encoded polypeptides of the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. its structure and/or biological activity). With particular reference to nucleic acid sequences, the term "substantially the same" is intended to refer to coding regions and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide that do not affect structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

A. Preparation of AVR1-CO39 Nucleic Acid Molecules, encoded Polypeptides and Antibodies Specific for the Polypeptides 1. Nucleic Acid Molecules AVR1-CO39 nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the genomic isolate having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.05 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.05 kb double-stranded molecule. A synthetic DNA molecule so constructed may then be cloned and amplified in an appropriate vector.

AVR1-CO39 genes also may be isolated from appropriate biological sources using methods known in the art. In one embodiment, a genomic clone has been isolated from a *M. grisea* strain 2539 cosmid library. In an alternative embodiment, a cDNA clone comprising one or more of the open reading frames of the genomic AVR1-CO39 locus may be isolated.

In accordance with the present invention, nucleic acids having the appropriate level sequence homology with part or all the coding regions of Sequence I.D. No. 1 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 2×SSC and 0.1% SDS; (4) 2 hours at 45–55° in 2×SSC and 0.1% SDS, changing the solution every 30 minutes. Alternatively, a modification of the Amasino hybridization protocol (Anal. Biochem. 152: 304–307) is preferred for use in the present invention and is described in greater detail in Example 1.

One common formula for calculating the stringency conditions required to achieve hybridization between nucleic acid molecules of a specified sequence homology (Sambrook et al., 1989):

$$T_m = 81.5° C. + 16.6 \log [Na+] + 0.41(\% G+C) - 0.63 (\% \text{formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable E. coli host cell.

AVR1-CO39 nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting AVR1-CO39 genes or MRNA in test samples of fungal isolates, e.g. by PCR amplification, or for the positive or negative regulation of expression of AVR1-CO39 genes at or before translation of the mRNA into proteins.

2. Proteins

The AVR1-CO39 genomic isolate described herein contains four open reading frames (ORF's 1–4), whose deduced amino acid sequences are set forth herein as Sequence I.D. No's. 2–5, respectively. Any one of these polypeptides may be prepared in a variety of ways, according to known methods. If produced in situ the polypeptides may be purified from appropriate sources, e.g., fungal isolates.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of AVR1-CO39-encoded polypeptides may be produced by expression in a suitable procaryotic or eucaryotic system. For example, part or all of a DNA molecule, such as the cDNA having Sequence I.D. No. 1, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The AVR1-CO39 polypeptide(s) produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The AVR1-CO39-encoded polypeptides of the invention, prepared by the aforementioned methods, may be analyzed according to standard procedures. Methods for analyzing the functional activity, i.e. ability to confer avirulence, are described in Example 1.

The present invention also provides antibodies capable of immunospecifically binding to polypeptides of the invention. Polyclonal or monoclonal antibodies directed toward any of the peptides encoded by the ORFs of AVR1-CO39 may be prepared according to standard methods. Monoclonal antibodies may be prepared according to general methods of Köhler and Milstein, following standard protocols. In a preferred embodiment, antibodies are prepared, which react immunospecifically with various epitopes of the AVR1-CO39-encoded polypeptides.

Polyclonal or monoclonal antibodies that immunospecifically interact with one or more of the polypeptides encoded by AVR1-CO39 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of the antibodies are described below.

B. Uses of AVR1-CO39 Nucleic Acids, Encoded Proteins and Antibodies

The potential of recombinant genetic engineering methods to enhance disease resistance in agronomically important plants has received considerable attention in recent years. Protocols are currently available for the stable introduction of genes into plants, as well as for augmentation of gene expression. The present invention provides nucleic acid molecules which, upon stable introduction into a recipient plant, or into an epiphytic microorganism, can enhance the plant's ability to resist pathogen attack. AVR1-CO39-encoded proteins of the invention may also be applied directly to a plant, to induce a disease defense response.

1. AVR1-CO39 Nucleic Acids

AVR1-CO39 nucleic acids (genomic clones or cDNAs) may be used for a variety of purposes in accordance with the present invention. The DNA, RNA, or fragments thereof may be used as probes to detect the presence of and/or expression of AVR1-CO39 genes. Methods in which AVR1-CO39 nucleic acids may be utilized as probes for such assays include, but are not limited to: (1) in situ hybridization; (2) Southern hybridization (3) northern hybridization; and (4) assorted amplification reactions such as polymerase chain reactions (PCR). The AVR1-CO39 nucleic acids of the invention may also be utilized as probes to identify homologs from other Magnaporthe isolates. As described above, AVR1-CO39 nucleic acids are also used to advantage to produce large quantities of substantially pure AVR1-CO39 proteins, or selected portions thereof.

Of perhaps greater significance, however, is the use of AVR1-CO39 nucleic acids to broaden the scope of resistance of rice cultivars carrying the CO39 resistance gene to pathogens other than *M. grisea* isolates carrying the AVR1-CO39 avirulence gene. For instance, in one embodiment of the invention, the AVR1-CO39 coding region is operably linked to a heterologous promoter, preferably one that is either generally pathogen inducible (i.e. inducible upon challenge by a broad range of pathogens) or wound inducible. Such promoters include, but are not limited to:

a) promoters of genes encoding lipoxygenases (preferably from plants, most preferably from rice, e.g., Peng et al., J. Biol. Chem. 269: 3755–3761, 1994; Peng et al., Abstract presented at the general meeting of the International Program on Rice Biotechnology, Malacca, Malaysia, Sep. 15–19, 1997);

b) promoters of genes encoding peroxidases (preferably from plants, most preferably from rice, e.g., Chittoor et al., Mol. Plant-Microbe Interactions 10: 861–871, 1997);

c) promoters of genes encoding hydroxymethylglutaryl-CoA reductase (preferably from plants, most preferably from rice, e.g., Nelson et al., Plant Mol. Biol. 25: 401–412, 1994);

d) promoters of genes encoding phenylalanine ammonia lyase (preferably from rice; e.g., Lamb et al., Abstract of the general meeting of the International Program on Rice Biotechnology, Malacca, Malaysia, Sep. 15–19, 1997)

e) promoters of genes encoding glutathione-S-transferase (preferably from plants, most preferably from rice, or alternatively, the PRP1 promoter from potato);

f) promoters from pollen-specific genes, such as corn Zmg13, which has been show to be expressed in rice transgenic pollen carrying the corn gene (Aldemita et al., Abstract of the general meeting of the International Program on Rice Biotechnology, Malacca, Malaysia, Sep. 15–19, 1997);

g) promoters from genes encoding chitinases (preferably from plants, most preferably from rice; e.g., Zhu & Lamb, Mol. Gen. Genet. 226: 289–296, 1991);

h) promoters from genes induced early (within 5 hours post-inoculation) in the interaction of *M. grisea* and rice (e.g., Bhargava & Hamer; Abstract B-10, 8th International Congress Molecular Plant Microbe Interactions, Knoxville, Tenn. Jul. 14–19, 1996);

i) promoters from plant (preferably rice) viral genes, either contained on a bacterial plasmid or on a plant viral vector, as described by Hammond-Kosack et al., Mol. Plant-Microbe Interactions 8: 181–185 (1994);

j) promoters from genes involved in the plant (preferably rice) respiratory burst (e.g., Groom et al., Plant J. 10(3): 515–522, 1996); and k) promoters from plant (preferably rice) anthocyanin pathway genes (e.g., Reddy, pp 341–352 in *Rice Genetics III*, supra; Reddy et al., Abstract of the general meeting of the International Program on Rice Biotechnology, Malacca, Malaysia, Sep. 15–19, 1997).

The chimeric gene is then used to transform rice cultivars that already carry the appropriate R gene. Upon wounding or challenge with a plant pathogen, the resulting transgenic plants would be induced to produce the AVR1-CO39 gene product, thereby triggering the R gene defense response. In this embodiment, care must be taken to avoid using a promoter that is induced by necrosis, since use of such a promoter could result in a self-perpetuating hypersensitive response that may be lethal to the plant (see, e.g., Kim et al., Proc. Natl. Acad. Sci. USA 91: 10445–10449, 1994).

In a preferred embodiment, a coding region of AVR1-CO39 (preferably the coding region corresponding to ORF3) is inserted into an expression vector in a microorganism that grows epiphytically on rice plants. A suspension of such recombinant microorganisms is sprayed on rice cultivars carrying the appropriate R gene. Upon pathogen attack, two levels of protection can occur: (1) the gene product produced by the recombinant epiphytes triggers an interaction on the plant surface that prevents further penetration by the pathogen (e.g., the fungal conidia develop appresoria, but do not develop penetration pegs); or (2) the gene product produced by the recombinant epiphytes is carried into the plant tissue at the wound site, where it interacts with the corresponding R gene product and induces an internal disease defense response. Thus, this pre-treatment confers resistance to Maganporthe isolates (and, presumably, other plant pathogens) which normally are virulent on those cultivars. This embodiment is described in greater detail in Example 3.

In connection with the use of epiphytic bacteria, it should be noted that bacterial and phage expression and delivery systems, such as those commercially available from InVitrogen, will be particularly useful. The bacterial system expresses a protein hybrid with pilin, such that the foreign protein is exposed on the exterior of the bacterium. The phage system also expresses a hybrid protein with coat component and exterior exposure of the foreign protein.

The AVR1-CO39 gene also may be used as a tool to identify and isolate its corresponding R gene. Thus, in a manner similar to that described for isolation of the tomato CF-9 gene for resistance to *Cladosporium fulvum* (Jones et al., Science 266: 789–793, 1994), the R gene in rice that corresponds to AVR1-CO39 can be isolated by transposon tagging: (1) AVR1-CO39 is transformed into, and constitutively expressed in a susceptible rice line; (2) the transgenic line is crossed with a resistant line that carries an identifiable transposon; (2) seedlings of F1 progeny constitutively expressing both the Avr gene and the corresponding R gene should die, thereby enabling a simple screening for live F1 progeny; (4) any live F1 progeny should be surviving by virtue of interruption of either the AVR1-CO39 transgene or the corresponding R gene, presumably by the transposon. The transposon, along with the gene it has interrupted, can thus be isolated.

2. AVR1-CO39 Proteins and Antibodies

Purified gene products of AVR1-CO39, or fragments thereof, may be used to produce polyclonal or monoclonal antibodies, which also may serve as sensitive detection reagents for the presence and accumulation of AVR1-CO39 polypeptides in transformed microbial epiphytes, transgenic plants, or other biological materials. Polyclonal or monoclonal antibodies immunologically specific for AVR1-CO39 polypeptides may be used in a variety of assays designed to detect and quantitate the proteins. Such assays include, but are not limited to: (1) flow cytometric analysis; (2) immunochemical localization of expressed proteins in cells or tissues; and (3) immunoblot analysis (e.g., dot blot, Western blot) of extracts from various cells and tissues. Additionally, as described above, antibodies can be used for purification of AVR1-CO39 polypeptides (e.g., affinity column purification, immunoprecipitation).

In a preferred embodiment, purified AVR1-CO39 polypeptides (most preferably from ORF3) are used as a pre-treatment or co-treatment to confer broad-spectrum pathogen resistance to rice cultivars carrying the CO39 R gene. Thus, in a manner similar to the above-described use of AVR1-CO39-expressing epiphytic microorganisms, a solution of the peptide is applied to the plants, and subsequent or concurrent wounding or inoculation with a pathogenic microorganism brings the peptide into contact with the R gene product, thereby stimulating a defense response. The inventors have experimentally demonstrated the feasibility of this approach, as described in detail in Example 4.

The following specific examples are provided to illustrate embodiments of the invention. They are not intended to limit the scope of the invention in any way.

EXAMPLE 1

Cloning and Analysis of AVR1-CO39

A chromosomal segment putatively containing the cultivar specificity gene, AVR1-CO39, was isolated from *M. grisea* strain 2539 using a map-based cloning approach, followed by chromosome walking (Leong et al., 1996). In this example we describe the identification, cloning and analysis of the AVR1-CO39 gene.

Methods

Hybridization protocol.

Hybridization methods were modified from Amasino (1986) "Acceleration of Nucleic Acid Hybridization Rate by Polyethylene Glycol", Analytical Biochemistry 152:304–307. The hybridization buffer was prepared according the Amasino protocol, but without the PEG and NaCl and with reduced concentrations of NaHPO4: 0.125M NaHPO4, 7% SDS, 50% formamide, 1.0 mM EDTA, pH 7.2. High stringency conditions were used (42° C., 16 h). Post hybridization washes were: one rinse with 2×SSC at room temperature; one wash in 2×SSC for 10 min at 65° C.; one wash in 2×SSC, 15 min at 65° C.; one final wash in 0.1×SSC, 0.1% SDS for 15 min at 65° C. The final washing conditions were of greater stringency than were the hybridization conditions, giving a $T_m$ of 68. Thus, greater than 95% homology would be required to maintain a hybrid. None of the post hybridization phosphate-containing buffers described in Amasino (1986) were employed.

Chromosome walking strategy.

A total genomic DNA library of *M. grisea* strain 2539 consisting of 5,194 clones was constructed in cosmid vector pMLF1 (Leong et al., 1994, supra) and pMLF2 (An et al., Gene 176: 93–96, 1996). Clones were templated individually as colony blots as well as in pools in which the DNA was restriction digested, electrophoresed and blotted. The latter blots were used initially to identify candidate pools containing hybridizing clones. Colony blots derived from these pools were then screened. Steps were performed using endclones prepared from the insert DNA by digesting the cosmid clones with ApaI, which does not digest the vector, and recircularizing the plasmid by ligation. This procedure results in a derivative containing DNA from each end of the insert (An et al., 1996 supra). Liberation of both ends of the insert from the vector was achieved by digesting with ApaI and NotI. The required endclone was then identified by virtue of its inability to hybridize with the previous cosmid in the walk.

Transformation of virulent strain Guy11 with cosmids within the AVR1-CO39 locus:

Cosmids from within the genetic interval containing AVR1-CO39 were introduced into Guy11 using the transformation protocol described in LEUNG et al. (1990). The procedure was modified as follows: After the protoplasts were incubated in complete medium (CM)+sorbitol, they were poured into 100 ml molten (45° C.) CM+20% sucrose agar. The agar was then poured into four petri plates. When the agar had solidified (1 h) it was overlaid with 15 ml of 1.5% water agar containing 800 µg/ml hygromycin B (300 µg/ml final concentration).

Creation of frameshift mutations in open reading frames at the AVR1-CO39 gene locus.

1.05 kb fragment was cloned into pBSKS II (pBSCO39) to make the first two clones. The mutant 1.05 kb fragments were then cloned into pCB1004 a hyg, vector from J. Sweigard (Dupont). Plasmids were linearized by NotI digestion and transformed into Guy11 protoplasts.

Initial frameshift mutations were created in ORFs 2 and 3 by digestion and religation as follows:

Frameshift in ORF2:

The AccI site at nucleotide (nt) position 499 was cut and the 2 nt 3' overhangs were trimmed off with T4 DNA polymerase. The site was then religated resulting in the removal of 4 bp or a net frameshift of −2. The nucleotide sequence changed from 5' CTAGACAGTCTACCTCTCT-GCCA3' (SEQ ID NO:9) to 5° CTAGACAGTACCTCTCT-GCCA 3' (SEQ ID NO:10).

Frameshift in ORFS 2 & 3:

The PflMI site at nt position 641 was cut and the 3 nt 3' overhang was trimmed off with T4 polymerase. A klenow-filled HindIII fragment containing the streptomycin resistance gene cassette from pHP45Ω (Prentki and Kritsch, Gene 29: 303, 1984) was ligated to the flush-ended PflMI fragment. The conserved HindIII site was then digested and religated. The net effect was the substitution of the 3 nt in the PflMI site with 4 nt from the HindIII site. This created a net frameshift of +1. The nucleotide sequence change was from 5' CCAGCAGCCAATGCTTGGAAAGATTG 3' (SEQ ID NO:11) to 5' CCAGCAGCCAAAGCTTTGGAAAGATTG 3' (SEQ ID NO:12).

In the ΔAccI construct, the peptide retains only 19 aa of its original sequence and is truncated after 36 aa. The native ORF2 peptide is 77 aa. In the ΔPfl construct, the ORF2 peptide sequence is almost unchanged except for the terminal 10 aa and the resulting peptide is 17 aa longer. ORF3, on the other hand, retains only 20 aa from its N-terminal and terminates after 31 aa.

The frameshift in ORF1 was created by "Quick Change" site-directed mutagenesis (Stratagene) using primers designed to introduce an extra G nucleotide after the ATG:

P1: CAACGTACTAGAAATGGAGTAATAAGTACC (SEQ ID NO:13)

P2: GGTACTTATTAGTCCATTTCTAGTACGTTG (SEQ ID NO:14)

The mutagenesis basically abolished the ORF completely.

Creation of ATG mutations in open reading frames at the AVR1-CO39 gene locus:

The 1.05 kb fragment containing AVR1-CO39 was cloned into pCB1004 and Quickchange mutagenesis (Stratagene) was used to make the following mutant constructs:

ΔORF1 (ATG→TTT): Start codon of ORF1 was eliminated by quick change mutagenesis using a primer with the mutant ATG sequence.

ΔORF3 (ATG→TTT): Start codon of ORF3 was eliminated by quick change mutagenesis using a primer with the mutant ATG sequence.

The following clone was made but the mutant allele has not yet been tested by transformation to determine the phenotype.

ΔORF2 (ATG→TTT): Start codon of ORF2 was eliminated by quick change mutagenesis using a primer with the mutant ATG sequence.

Results

As mentioned above, a gene conferring cultivar-specific interactions with rice cultivar CO39 was isolated from *M. grisea* strain 2539 using a map-based cloning approach, followed by a 20-step chromosome walk. The AVR1-CO39 locus was delimited to a 1.05 kb region by subcloning and transformation of Guy11, a strain normally virulent on CO39, to avirulence. The nucleotide sequence of this 1.05 kb region of Chromosome 1 is set forth below

```
(5'→3')                                                       SEQ ID NO: 1
GATCTGTAAA TTACATATAT TTATTTTGCC GCATTTTGCT AACCGCCTAT

TCTTTTTAAA ATTTTAACGA TTAAGAACGC AATTCAATTT TGCGTTCTAC

ACAAATTAAC AATTCGTCCA AAAGAGGTAT TTAAGCGAAG ATTTGGCATT

TTTTTAATCC ATTTTTAAAA AAATACATCT GCTTTAACCC ACCTTTGCCA

AGGGTACCCG GCTAGCATAG CCTTCGTTAC CAAAAACGGC TAAAGCTGTC

GATCTATACT ACATTCGGCG CTCTGAACAA CTAAGCAACA GCGAGGAGAT

T5
CACACCCTAA ATCATGCTGC TAGTAATGCG ATATAATGGC CAAACAACGT

ORF1→
ACTAGAAATG ACTAATAAGT ACCCAGTCAA GTCAACTTGC TGTAGTATTA

←ORF5                              ORF2→
TATTTAACGA AGCGTCCATT TACTGCCACG GCAAGTTTAT CAATGGGACC

T1
AGTGTTCTCC CTCCTCTGGA CAACTCAGTT CTTTGCAAAC GCTAGACAGT

CTACCTCTCT GCCACCATTT TTACTTTTCA AAAATTTACT CCTTGCCGCT

T4                    ORF3→
ACTGAAACTT CTACAATTGA AAGAGCCCAC AATGAAAGTC CAAGCTACAT

TCGCCACCCT TATCGCCCTT GCGGCTTACT TTCCAGCAGC CAATGCTTGG

T2
AAAGATTGCA TCATCCAACG TTATAAAGAC GGCGATGTCA ACAACATATA

TACTGCCAAT AGGAACGAAG AGATAACTAT TGAGGAATAT AAAGTCTTCG

ORF6→      ←ORF4
TTAATGAGGC CTGCCATCCC TACCCAGTTA TACTTCCCGA CAGATCGGTC

T3
CTTTCTGGCG ATTTTACATC AGCTTACGCT GACGACGATG AGTCTTGTTG

T6                          ORF7→
ATCAATAAGA GTCCAGGTTG AAAAATTCGC CACCATGGTA ATAGAGGGTT

ATTTATCTCG GAATAGCAGC CGTGTGTGCA ATTATCACGG CTGTTCCTCT

GCGATAGGGA TATTAGAAGC AGGACAAATT TACGGCAATA GCAACCAATT

GTCCTTGTCT ATGGATTCGC CCGTCGAATG GAGGCGACGG CGGATCC
```

DNA sequence analysis revealed four small open reading frames of 45, 77, 89 and 69 amino acids in length (ORF1, ORF2, ORF3, ORF4, respectively, as shown on SEQ ID No. 1 above). The amino acid sequences encoded by the four open reading frames are set forth below as Sequence ID No's. 2, 3, 4 and 5, respectively. Three other open reading frames were also identified (ORFS 5, 6, and 7, set forth below as SEQ ID NOS: 6, 7 and 8, respectively.

AVR1-CO39 ORF1 (SEQ ID NO: 2)

MTNKYPVKST CCSIIFNEAS IYCQGKFING TSVLPPLDNS VLCKR

AVR1-CO39 ORF2 (SEQ ID NO: 3)

MGPVFSLLWT TQFFANARQS TSLPPFLLFK NLLLAATETS TIERAHNESP SYIRHPYRPC GLLSSSQCLE RLHHPTL

AVR1-CO39 ORF3 (SEQ ID NO: 4)

MKVQATFATL IALAAYFPAA NAWKDCIIQR YKDGDVNNIY TANRNEEITI EEYKVFVNEA CHPYPVILPD RSVLSGDFTS AYADDDESC

AVR1-CO39 ORF4 (SEQ ID NO: 5)

MAGLINEDFI FLNSYLFVPI GSIYVVDIAV FITLDDAIFP SIGCWKVSRK GDKGGECSLD FHCGLFQL

AVR1-CO39 ORF5 (SEQ ID NO: 6)

MDASLNIILQ QVDLTGYLLV ISSTLFGHYI ALLAA

AVR1-CO39 ORF6 (SEQ ID NO: 7)

MRPAIPTQLY FPTDRSFLAI LHQLTLTTMS LVDQ

AVR1-CO39 ORF7 (SEQ ID NO: 8)

MVIEGYLSRN SSRVCNYHGC SSAIGILEAG QIYGNSNQLS LSMDSPVEWR RRRI (continues beyond cloned DNA)

The sequence surrounding the ATG of ORP3 matched four out of five of the conserved bases found in fungal translation start sites and contained a hydrophobic amino terminus punctuated by a lysine in position 2, and two putative cleavage sites for removal of the signal peptide. A fourth open reading frame (ORF4) was identified on the opposite strand. However, the sequence surrounding that ATG contained only two matches with the fungal translation start site consensus sequence.

Site-directed mutations in ORF1, ORF2 and ORF3 were created in order to assess the roles of these ORFS in conferring avirulence. The translation start codon of each ORF was converted from ATG to TTT. In ORFs 1 and 3, these mutations led to loss of avirulence. Frameshift mutations in ORF1 and ORF3 also led to a loss of avirulence, while the frameshift mutation of ORF 2 did not. Taken together, these data indicate a role for ORF1 and ORF3 in conferring avirulence to *M. grisea* strain 2539 on rice cultivar CO39.

The absence of a splice site and a lariat sequence, as well as any putative TATA element immediately upstream of the ATG of ORF1 may indicate that ORF1 overlaps sequences critical to the promotion of transcription of AVR1-CO39.

EXAMPLE 2

Distribution of AVR1-CO39 Homologs in Diverse Isolates of *Magnaporthe grisea*

The distribution of AVR1-CO39 homologs was investigated by probing a large sample of host-specific. forms of *M. grisea* with a segment of AVR1-CO39 DNA, using hybridization conditions such as those described in Example 1. The results of this survey indicate that isolates infecting rice, Digitaria and wheat largely lack homologs of Avr-CO39. However, homologs of the gene were commonly found in Elutine (Setaria)-infecting isolates. Moreover, a detailed analysis of the AVR1-CO39 locus from virulent rice isolate Guy 11 indicated that at least 20 Kb of DNA corresponding to and containing the AVR1-CO39 locus of isolate 2539 was absent.

EXAMPLE 3

Improved Resistance to *M. grisea* Infection in Rice Plants Sprayed with Bacterial Epiphytes expressing ORF 3 of AVR1-CO39

The ORF3 of AVR1-CO39 described in Example 1 was transferred into a pET expression vector in *Escherichia coli*. A suspension containing the transformed *E. coli* was sprayed onto leaves of rice plants carrying the corresponding R gene for AVR1-CO39. The plants were then inoculated with *M. grisea* isolate Guy 11, which is a virulent strain on the plant cultivars tested. As a control, plants were sprayed with an *E. coli* suspension which did not contain the ORF-3 encoding plasmid, then inoculated with isolate Guy 11.

Inoculated plants pre-treated with the ORF3-expressing *E. coli* displayed reduced lesion size and number as compared to inoculated control plants pre-treated with *E. coli* lacking the ORF3-expressing plasmid. These data support the role of ORF3 in conferring avirulence in *M. grisea*.

EXAMPLE 4

Improved Resistance to *M. grisea* Infection in Rice Plants Sprayed with Protein Encoded by ORF 3 of AVR1-CO39

The ORF3 of AVR1-CO39 described in Example 1 was transferred into a pET expression vector in *Escherichia coli*. Protein extracts from IPTG-induced *E. coli* cells carrying either the pET vector alone (control) or the pET-ORF3 construct were tested for their effects on virulence. The cellular protein extracts were concentrated by ammonium sulfate precipitation. Cultivar CO39 was inoculated with virulent *M. grisea* strain Guy11 in combination with the concentrated protein extract to give $5 \times 10^5$ conidia and 20 mg total protein extract in 10 ml sterile water.

Inoculated plants co-treated with the ORF3-containing protein extract displayed reduced lesion size and number as compared to inoculated control plants co-treated with protein extract lacking ORF3. These data further support the role of ORF3 in conferring avirulence in *M. grisea*.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. An isolated nucleic acid molecule encoding SEQ ID NO:4.

2. The nucleic acid molecule of claim 1, comprising nucleotides 582–850 of SEQ ID NO:1.

3. The nucleic acid molecule of claim 1, comprising SEQ ID NO:1.

4. A vector for transforming cells, comprising the nucleic acid molecule of claim 1.

5. A fungal or bacterial cell transformed with the vector of claim 4.

6. The cell of claim 5, wherein th cell is an epiphytic bacterial cell.

7. A transgenic epiphytic bacterium comprising a construct comprising an isolated nucleic acid molecule that encodes SEQ

SEQUENCE LISTING

<160> NUMBER OF SEQ ID NOS: 14

<210> SEQ ID NO 1
<211> LENGTH: 1047
<212> TYPE: DNA
<213> ORGANISM: Magnaporthe grisea

<400> SEQUENCE: 1

```
gatctgtaaa ttacatatat ttattttgcc gcattttgct aaccgcctat tctttttaaa     60
attttaacga ttaagaacgc aattcaattt tgcgttctac acaaattaac aattcgtcca    120
aaagaggtat ttaagcgaag atttggcatt tttttaatcc atttttaaaa aaatacatct    180
gctttaaccc acctttgcca agggtacccg gctagcatag ccttggttac caaaaacggc    240
taaagctgtc gatctatact acattcggcg ctctgaacaa ctaagcaaca gcgaggagat    300
cacaccctaa atcatgctgc tagtaatgcg atataatggc caaacaacgt actagaaatg    360
actaataagt acccagtcaa gtcaacttgc tgtagtatta tatttaacga agcgtccatt    420
tactgccagg gcaagtttat caatgggacc agtgttctcc ctcctctgga caactcagtt    480
ctttgcaaac gctagacagt ctacctctct gccaccattt ttacttttca aaaatttact    540
ccttgccgct actgaaactt ctacaattga aagagcccac aatgaaagtc caagctacat    600
tcgccaccct tatcgccctt gcggcttact ttccagcagc caatgcttgg aaagattgca    660
tcatccaacg ttataaagac ggcgatgtca acaacatata tactgccaat aggaacgaag    720
agataactat tgaggaatat aaagtcttcg ttaatgaggc ctgccatccc tacccagtta    780
tacttcccga cagatcggtc ctttctggcg attttacatc agcttacgct gacgacgatg    840
agtcttgttg atcaataaga gtccaggttg aaaaattcgc caccatggta atagagggtt    900
atttatctcg gaatagcagc cgtgtgtgca attatcacgg ctgttcctct gcgataggga    960
tattagaagc aggacaaatt tacggcaata gcaaccaatt gtccttgtct atggattcgc   1020
ccgtcgaatg gaggcgacgg cggatcc                                       1047
```

<210> SEQ ID NO 2
<211> LENGTH: 45
<212> TYPE: PRT
<213> ORGANISM: Magnaporthe grisea

<400> SEQUENCE: 2

```
Met Thr Asn Lys Tyr Pro Val Lys Ser Thr Cys Cys Ser Ile Ile Phe
 1               5                  10                  15

Asn Glu Ala Ser Ile Tyr Cys Gln Gly Lys Phe Ile Asn Gly Thr Ser
            20                  25                  30

Val Leu Pro Pro Leu Asp Asn Ser Val Leu Cys Lys Arg
        35                  40                  45
```

<210> SEQ ID NO 3
<211> LENGTH: 77
<212> TYPE: PRT
<213> ORGANISM: Magnaporthe grisea

<400> SEQUENCE: 3

```
Met Gly Pro Val Phe Ser Leu Leu Trp Thr Thr Gln Phe Phe Ala Asn
 1               5                  10                  15

Ala Arg Gln Ser Thr Ser Leu Pro Pro Phe Leu Leu Phe Lys Asn Leu
            20                  25                  30
```

-continued

```
Leu Leu Ala Ala Thr Glu Thr Ser Thr Ile Glu Arg Ala His Asn Glu
        35                  40                  45

Ser Pro Ser Tyr Ile Arg His Pro Tyr Arg Pro Cys Gly Leu Leu Ser
    50                  55                  60

Ser Ser Gln Cys Leu Glu Arg Leu His His Pro Thr Leu
65                  70                  75

<210> SEQ ID NO 4
<211> LENGTH: 89
<212> TYPE: PRT
<213> ORGANISM: Magnaporthe grisea

<400> SEQUENCE: 4

Met Lys Val Gln Ala Thr Phe Ala Thr Leu Ile Ala Leu Ala Ala Tyr
 1               5                  10                  15

Phe Pro Ala Ala Asn Ala Trp Lys Asp Cys Ile Ile Gln Arg Tyr Lys
            20                  25                  30

Asp Gly Asp Val Asn Asn Ile Tyr Thr Ala Asn Arg Asn Glu Glu Ile
        35                  40                  45

Thr Ile Glu Glu Tyr Lys Val Phe Val Asn Glu Ala Cys His Pro Tyr
    50                  55                  60

Pro Val Ile Leu Pro Asp Arg Ser Val Leu Ser Gly Asp Phe Thr Ser
65                  70                  75                  80

Ala Tyr Ala Asp Asp Asp Glu Ser Cys
                85

<210> SEQ ID NO 5
<211> LENGTH: 68
<212> TYPE: PRT
<213> ORGANISM: Magnaporthe grisea

<400> SEQUENCE: 5

Met Ala Gly Leu Ile Asn Glu Asp Phe Ile Phe Leu Asn Ser Tyr Leu
 1               5                  10                  15

Phe Val Pro Ile Gly Ser Ile Tyr Val Val Asp Ile Ala Val Phe Ile
            20                  25                  30

Thr Leu Asp Asp Ala Ile Phe Pro Ser Ile Gly Cys Trp Lys Val Ser
        35                  40                  45

Arg Lys Gly Asp Lys Gly Gly Glu Cys Ser Leu Asp Phe His Cys Gly
    50                  55                  60

Leu Phe Gln Leu
65

<210> SEQ ID NO 6
<211> LENGTH: 35
<212> TYPE: PRT
<213> ORGANISM: Magnaporthe grisea

<400> SEQUENCE: 6

Met Asp Ala Ser Leu Asn Ile Ile Leu Gln Gln Val Asp Leu Thr Gly
 1               5                  10                  15

Tyr Leu Leu Val Ile Ser Ser Thr Leu Phe Gly His Tyr Ile Ala Leu
            20                  25                  30

Leu Ala Ala
        35

<210> SEQ ID NO 7
<211> LENGTH: 34
<212> TYPE: PRT
```

<213> ORGANISM: Magnaporthe grisea

<400> SEQUENCE: 7

Met Arg Pro Ala Ile Pro Thr Gln Leu Tyr Phe Pro Thr Asp Arg Ser
1               5                   10                  15
Phe Leu Ala Ile Leu His Gln Leu Thr Leu Thr Thr Met Ser Leu Val
            20                  25                  30
Asp Gln

<210> SEQ ID NO 8
<211> LENGTH: 54
<212> TYPE: PRT
<213> ORGANISM: Magnaporthe grisea

<400> SEQUENCE: 8

Met Val Ile Glu Gly Tyr Leu Ser Arg Asn Ser Ser Arg Val Cys Asn
1               5                   10                  15
Tyr His Gly Cys Ser Ser Ala Ile Gly Ile Leu Glu Ala Gly Gln Ile
            20                  25                  30
Tyr Gly Asn Ser Asn Gln Leu Ser Leu Ser Met Asp Ser Pro Val Glu
        35                  40                  45
Trp Arg Arg Arg Arg Ile
    50

<210> SEQ ID NO 9
<211> LENGTH: 23
<212> TYPE: DNA
<213> ORGANISM: Magnaporthe grisea

<400> SEQUENCE: 9
ctagacagtc tacctctctg cca                                           23

<210> SEQ ID NO 10
<211> LENGTH: 21
<212> TYPE: DNA
<213> ORGANISM: Magnaporthe grisea

<400> SEQUENCE: 10
ctagacagta cctctctgcc a                                             21

<210> SEQ ID NO 11
<211> LENGTH: 26
<212> TYPE: DNA
<213> ORGANISM: Magnaporthe grisea

<400> SEQUENCE: 11
ccagcagcca atgcttggaa agattg                                        26

<210> SEQ ID NO 12
<211> LENGTH: 27
<212> TYPE: DNA
<213> ORGANISM: Magnaporthe grisea

<400> SEQUENCE: 12
ccagcagcca aagctttgga aagattg                                       27

<210> SEQ ID NO 13
<211> LENGTH: 30
<212> TYPE: DNA
<213> ORGANISM: Magnaporthe grisea

<400> SEQUENCE: 13

-continued

```
caacgtacta gaaatggagt aataagtacc                              30

<210> SEQ ID NO 14
<211> LENGTH: 30
<212> TYPE: DNA
<213> ORGANISM: Magnaporthe grisea

<400> SEQUENCE: 14
ggtacttatt agtccatttc tagtacgttg                              30
```